United States Patent
Lee et al.

(10) Patent No.: US 9,089,285 B2
(45) Date of Patent: Jul. 28, 2015

(54) ENERGY EXPENDITURE COMPUTATION BASED ON ACCELEROMETER AND HEART RATE MONITOR

(71) Applicant: Salutron, Inc., Fremont, CA (US)

(72) Inventors: Yong Jin Lee, Palo Alto, CA (US); Eddy Hui, Kowloon (HK); Kaiping Chen, San Jose, CA (US)

(73) Assignee: Salutron, Inc., Fremont, CA (US)

( * ) Notice: Subject to any disclaimer, the term of this patent is extended or adjusted under 35 U.S.C. 154(b) by 0 days.

(21) Appl. No.: 13/755,760

(22) Filed: Jan. 31, 2013

(65) Prior Publication Data

US 2014/0213920 A1 Jul. 31, 2014

(51) Int. Cl.
*A61B 5/22* (2006.01)
*A61B 5/11* (2006.01)
*A61B 5/024* (2006.01)
*A61B 5/0245* (2006.01)
*A61B 5/00* (2006.01)

(52) U.S. Cl.
CPC ............. *A61B 5/1118* (2013.01); *A61B 5/0245* (2013.01); *A61B 5/02438* (2013.01); *A61B 5/222* (2013.01); *A61B 5/4866* (2013.01); *A61B 5/681* (2013.01)

(58) Field of Classification Search
None
See application file for complete search history.

(56) References Cited

U.S. PATENT DOCUMENTS

| | | | |
|---|---|---|---|
| 7,643,873 B2 * | 1/2010 | Chan | 600/520 |
| 8,386,008 B2 * | 2/2013 | Yuen et al. | 600/382 |
| 8,827,906 B2 * | 9/2014 | Yuen et al. | 600/301 |
| 2001/0049470 A1 * | 12/2001 | Mault et al. | 600/300 |
| 2007/0051369 A1 | 3/2007 | Choi et al. | |
| 2007/0282176 A1 | 12/2007 | Shimada et al. | |
| 2011/0152637 A1 | 6/2011 | Kateraas et al. | |
| 2012/0083705 A1 | 4/2012 | Yuen et al. | |
| 2012/0274508 A1 | 11/2012 | Brown et al. | |

FOREIGN PATENT DOCUMENTS

| | | | |
|---|---|---|---|
| EP | 1226784 A1 | 7/2002 | |
| EP | 1849407 A1 | 10/2007 | |

OTHER PUBLICATIONS

Johannes, Laura, "Burn Notice: How Accurate Are Devices That Track Calories Used?," The Wall Street Journal (WSJ.com), Jun. 23, 2009, 2 pages.

"How Does BodyMedia Fit Count Calories?," printed from BodyMedia.com [http://www.bodymedia.com/More-Details?whence=] on Jan. 23, 2013, 3 pages.

(Continued)

*Primary Examiner* — Paula J Stice
(74) *Attorney, Agent, or Firm* — Vierra Magen Marcus LLP (57) ABSTRACT

An activity monitor such as a wrist-worn device has an accelerometer which continuously detects motion of the user. The activity monitor also has an on-demand heart rate monitor which is activated by the user touching it from time to time. A calorie expenditure based on the motion of the user can be modified based on a heart rate measurement. Further, a determination can be made as to whether the user has made repetitive motions for a period of time. If the repetitive motions are detected, a calorie expenditure based on the heart rate is determined and compared to the calorie expenditure based on the user motion, and the higher value prevails. A situation is avoided in which the activity monitor underestimates the calories expended, such as when the user is exercising strenuously but the accelerometer indicates relatively little motion, e.g., during strength training.

13 Claims, 7 Drawing Sheets

(56) References Cited

OTHER PUBLICATIONS

Zhang, Kuan, et al., "Improving Energy Expenditure Estimation for Physical Activity," Medicine & Science in Sports & Exercise, vol. 36, No. 5, May 2004, 7 pages.

Zhang, Kuan, et al., "Measurement of Human Daily Physical Activity," Obesity Research, vol. 11, No. 1, Jan. 2003, 8 pages.

"Testing the Phillips DirectLife Accelerometer," Weightology Weekly, [http://weightology.net/weightologyweekly/?page_id=646], printed on Jan. 23, 2013, 4 pages.

Andre, David, et al., "Recent Advances in Free-Living Physical Activity Monitoring: A Review," Journal of Diabetes Science and Technology, vol. 1, Issue 5, Sep. 2007, 8 pages.

International Search Report & the Written Opinion of the International Searching Authority dated Jun. 5, 2014.

* cited by examiner

| Activity | Intensity | CBR |
|---|---|---|
| A | 1 | 200 |
|   | 2 | 250 |
|   | 3 | 300 |
| B | 1 | 400 |
|   | 2 | 500 |
|   | 3 | 600 |

ENERGY EXPENDITURE COMPUTATION BASED ON ACCELEROMETER AND HEART RATE MONITOR

BACKGROUND

Activity monitors have become popular as a tool for promoting exercise and a healthy lifestyle. An activity monitor can include an accelerometer which can measure motions such as steps taken while walking or running, and estimate an amount of calories used. Moreover, user-specific information such as age, gender, height and weight can be used to tailor the estimate to the user. Such monitors can be worn on the wrist, belt or arm, for instance, or carried in the pocket. The monitor can be worn during an intended workout period or as a general, all day, free living monitor, where the user may perform specific exercises at some times while going about their daily activities at other times, e.g., including sitting, standing and sleeping.

An activity monitor can include a heart rate monitor. Heart rate monitors are also used to monitor individuals, typically during an exercise session in which the user tries to maintain a target heart rate. Some ECG-based monitors are worn on a chest strap, where the electrodes of the monitor are constantly in contact with the body and can therefore continuously determine heart rate. Heart rate data can be transmitted from the chest strap to a display such as on a wrist worn device for easy viewing by the user. Other monitors are wrist-worn, for example, and only determine the heart rate on demand, when the user touches electrodes on the monitor or provides another manual control input. The electrodes can be buttons on part of the watch case, for instance. In one approach, an additional ECG electrode contacts the user on the back of the watch. Other monitors use electrodes attached to gloves, on armbands or on small devices the user touches.

SUMMARY

As described herein, an activity monitor is provided for detecting an amount of energy, e.g., calories, burned by a user over a period of time. The activity monitor includes an accelerometer and an on-demand heart rate monitor. A calorie expenditure is computed based on the motion of the user as determined by the accelerometer, and this calorie expenditure can be modified from time to time when the on-demand heart rate monitor is activated. The monitor can increase the calorie expenditure when the heart rate monitor indicates the user is exercising strenuously but the accelerometer indicates relatively little motion by the user such as during strength training exercises. A situation is avoided in which the activity monitor underestimates the calories expended.

In one approach, an activity monitor includes an accelerometer, an on-demand heart rate monitor and a processor. The accelerometer is adapted to measure activity of a user. The on-demand heart rate monitor is adapted to measure a heart rate of the user in response to the user touching the heart rate monitor. The processor is in communication with the accelerometer and the on-demand heart rate monitor. The processor determines an activity-based energy expenditure based on the activity and a heart rate-based energy expenditure based on the heart rate and provides an output energy expenditure based on a comparison of the heart rate-based energy expenditure with the activity-based energy expenditure.

This summary is provided to introduce a selection of concepts in a simplified form that are further described below in the description. This summary is not intended to identify key features or essential features of the claimed subject matter, nor is it intended to be used to limit the scope of the claimed subject matter.

BRIEF DESCRIPTION OF THE DRAWINGS

In the drawings, like-numbered elements correspond to one another.

DETAILED DESCRIPTION

An activity monitor is provided for detecting an amount of energy, e.g., calories, burned by a user over a period of time.

Figures 1A, 1B, 1C:
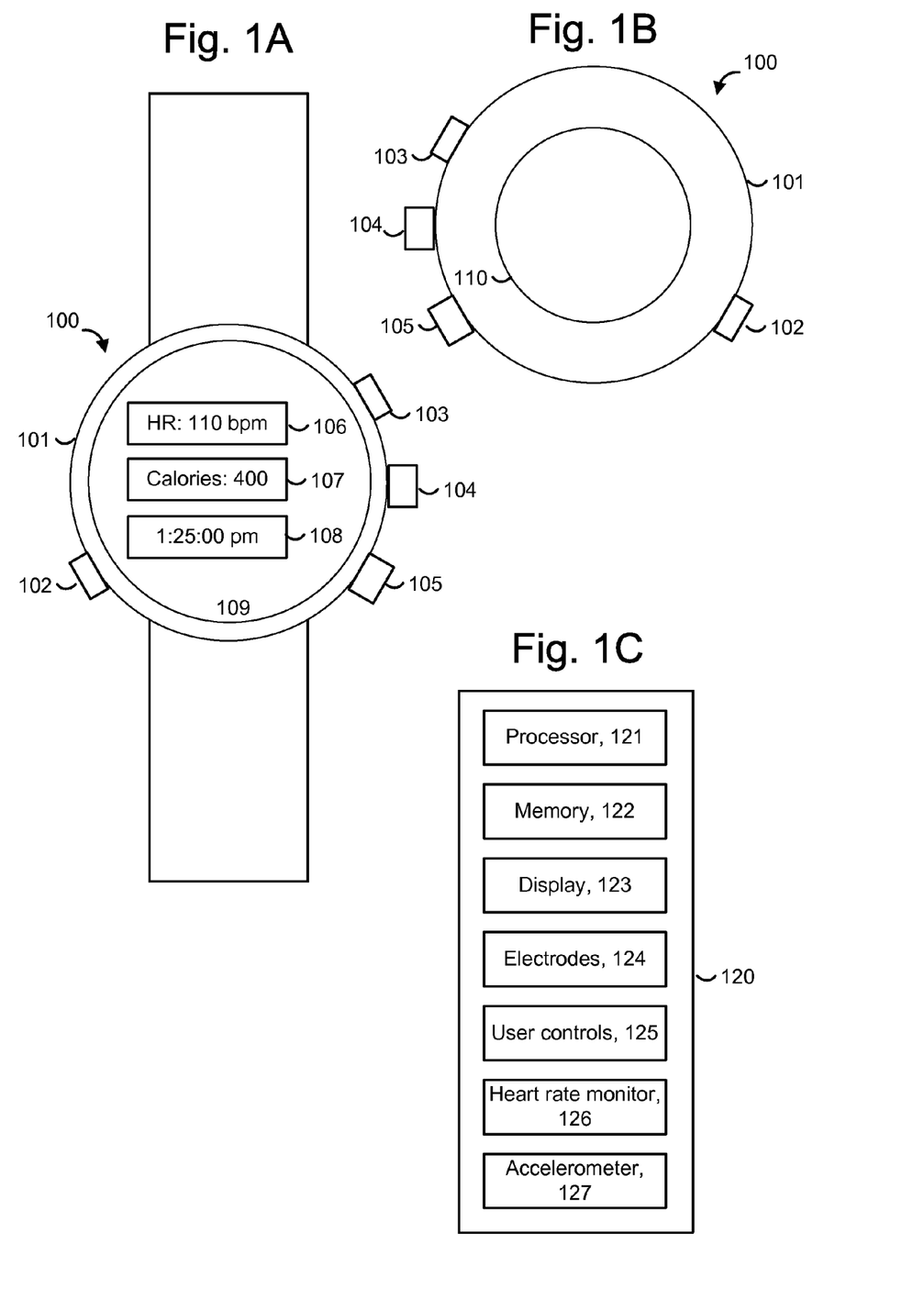
FIG. 1A depicts a front view of an example activity monitor.
FIG. 1B depicts a rear view of the activity monitor of FIG. 1A.
FIG. 1C depicts an example block diagram of the activity monitor of FIG. 1A.

FIG. 1A depicts a front view of an example activity monitor. The activity monitor 100 can be a wristwatch type device comprising a watch face and a strap for wearing around the wrist in this example, but other implementations are possible. For example, such monitors can be worn on the belt, head, chest, arm or carried in the pocket. A monitor could also include multiple components which are attached to different parts of the body. For example, the different components can include accelerometers which are attached to different parts of the body, e.g., the arm and leg, to gain a more complete understanding of the user's activity. The activity monitor 100 includes a case 101, a crown 104, a mode select button 105 and electrodes 102 and 103. A display device 109 includes a region 106 which depicts a heart rate (HR) (e.g., 110 beats per minutes or bpm), a region 107 which depicts an amount of calories (e.g., 400 calories) consumed in a monitoring session, and a region 108 which depicts a time of day (e.g., 1:25:00 pm). The mode select button 105 may allow the user to activate different operational modes and to input user-specific information such as age, gender, height, weight or body mass index.

The activity monitor can include an on-demand heart rate monitor which determines the heart rate only in response to a specific manual user action. For example, an ECG-based monitor can be provided in which the heart rate is determined when the user touches the electrodes 102 and 103. An additional electrode 110 on the back of the activity monitor also contacts the user's skin to complete the ECG circuit as depicted in FIG. 1B. As another example, ultrasonic based monitors determine the heart rate when the user activates a button. Optical sensors can also be used to determine heart rate. These types of monitors are popular since they do not require an electrode-carrying chest strap. They allow the user to check his heart rate from time to time rather than continuously.

FIG. 1C depicts an example block diagram of the activity monitor of FIG. 1A. In this example, the circuitry 120 includes a processor 121, a memory 122, a display 123, electrodes 124, user controls 125, a heart rate monitor 126 and an accelerometer 127, such as a three-axis accelerometer. The processor and memory 122 can be part of a micro-processor controller. The diagram is meant to provide a high level understanding of the activity monitor. Specific implementations can take many forms. For example, heart rate signals can be subject to analog signal processing, analog to digital conversion, time domain processing, conversion to the frequency domain such using a Fast Fourier Transform and frequency domain processing. Accelerometer signals can be similarly processed.

The processor may be in communication with each of the other components and transmit signals to them and/or receive signals from them. The memory can store code which is executed by the processor to perform the functionality described herein. The memory is an example of a computer-readable storage apparatus having computer-readable software embodied thereon for programming a processor to perform a method. For example, non-volatile memory can be used. Volatile memory such as a working memory of the processor can also be used. The display 123 can represent circuitry used to provide the display device 109 of FIG. 1A, for instance. The electrodes 124 can represent circuitry used to provide the electrodes 102 and 103 of FIG. 1A, for instance. The heart rate monitor determines an instantaneous heart rate of a user who is touching the electrodes. The accelerometer takes acceleration readings at a prescribed rate such as multiple times per second.

Figure 2A:
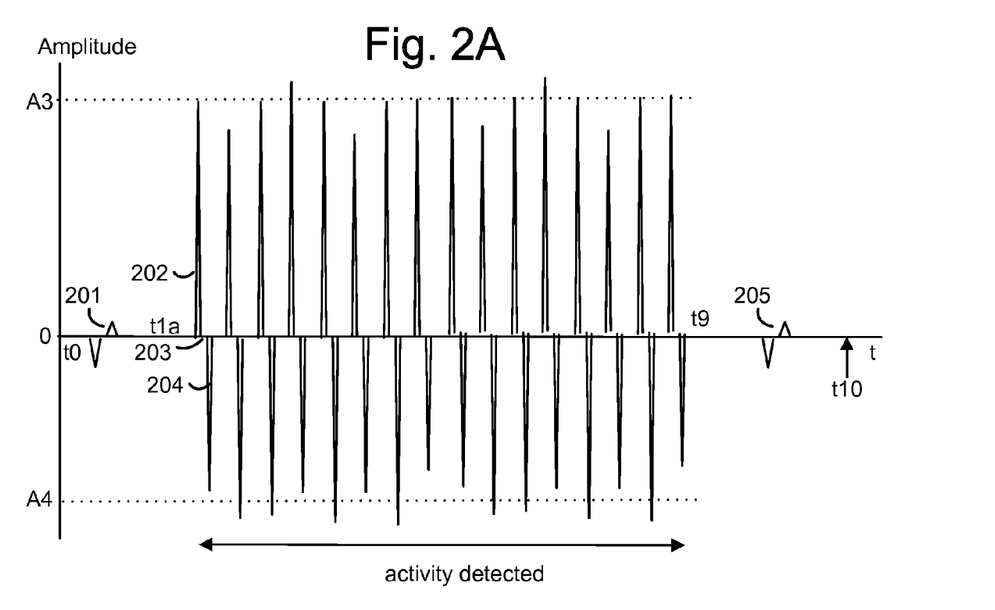
FIG. 2A depicts example accelerometer readings during vigorous exercise such as running, showing a relatively high amount of activity, where a repetitive pattern is detected.

FIG. 2A depicts example accelerometer readings during vigorous exercise such as running, showing a relatively high amount of activity, where a repetitive pattern is detected. An accelerometer has the ability to measure acceleration in one, two or three directions, such as along the x, y and z axes of a Cartesian coordinate system. The magnitude of acceleration can be determined as well. In some cases, the acceleration is not recorded unless it exceeds threshold. A movement of a user is represented by acceleration readings, e.g., along the x, y and z axes. In one approach, each movement results in an activity count. Generally, the level of activity of a user over time can be determined based on the acceleration readings. For example, amplitude, frequency and zero-crossings of the acceleration can be used to determine a level of activity. Higher amplitudes, frequencies and zero-crossings are associated with a higher activity level.

In the example provided, time extends on the horizontal axis and amplitude is on the vertical axis. The amplitude could represent a component (Ax, Ay, Az) along one of the x, y and z axes of an amplitude vector, or the amplitude could represent the magnitude of an amplitude vector, e.g., the square root of $Ax^2+Ay^2+Az^3$. The amplitude extends generally between A4 and A3. Acceleration readings 201 and 205 indicate small movements. Subsequent acceleration readings such as 202 and 204, with a zero crossing 203 between them, indicate larger, relatively high frequency movements. For example, the user may be running. The larger, relatively high frequency movements extend from t1a to t9.

In some cases, the type of exercise that a user is performing can be detected based on characteristics of the accelerometer readings. For example, a training process may be performed in which the user performs specified exercises and the resulting accelerometer readings are recorded. Accelerometer readings from a subsequent exercise period can be compared to the recorded accelerometer readings (signatures) to identify the exercise being performed, as well as a pace of the exercise based on the frequency of movement. For example, it may be determined that a user is running at 3 miles per hour. The type of exercise which is performed and the pace of the exercise can further be correlated with a rate of calories burned by the user based on scientific studies which have been published. The rate of calories burned can be tailored to a particular user based on factors such as age, gender, height and weight. This information can all be encompassed within control logic of the processor 121 using appropriate formulas and tables.

A time point t10 is an example time at which a user obtains a heart rate. In an example scenario, the user obtains a heart rate shortly after completing an intense exercise session.

Figure 2B:
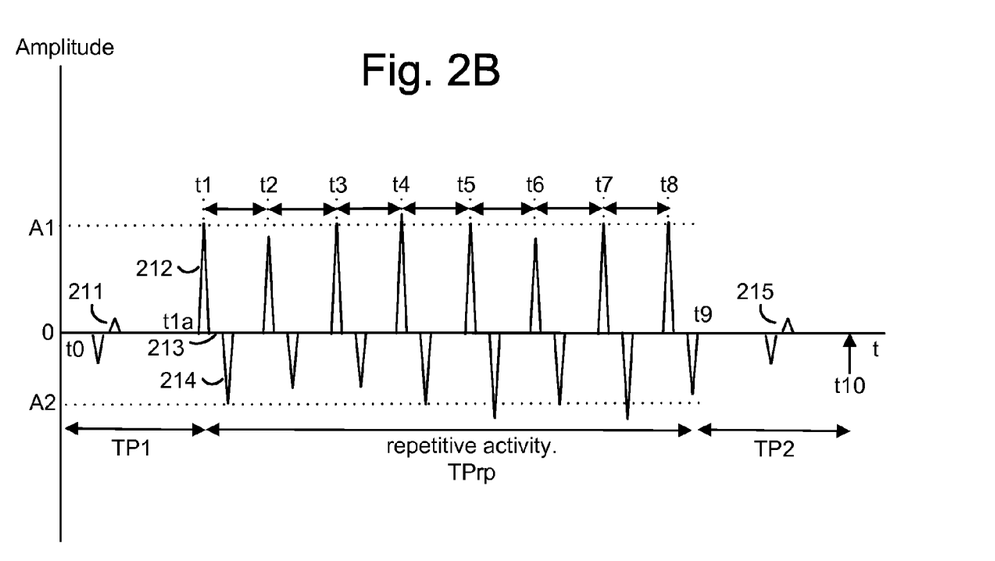
FIG. 2B depicts example accelerometer readings during strength training exercises, showing a relatively low amount of activity, where a repetitive pattern is detected.

FIG. 2B depicts example accelerometer readings during strength training exercises, showing a relatively low amount of activity, where a repetitive pattern is detected. The amplitude and time scales are the same as in FIG. 2A. The amplitude extends generally between A1 and A2. Acceleration readings 211 and 215 indicate small movements. Subsequent acceleration readings such as 212 and 214, with a zero crossing 213 between them, indicate low-moderate amplitude and frequency movements which extend from t1a to t9. The acceleration peaks are at t1-t8. A period of repetitive activity TPrp extends from t1a-t9. Remaining periods in which repetitive activity is not detected include TP1 (t0-t1a) and TP2 (t9-t10).

This acceleration profile may occur when the user is performing strength training. For example, strength training can involve lifting weights or performing calisthenics such as pushups or chin ups. These types of exercises can result in relatively low acceleration readings since the activity monitor may move very little or not at all. For example, a wrist worn activity monitor would not move very much during pushups or chin ups. However, the user is performing strenuous exercise using the large muscles of the body, so the heart rate will increase significantly. A calorie measuring technique which relied only on the acceleration readings would significantly underestimate the calorie consumption, leading to incorrect information for the user.

Figure 2C:
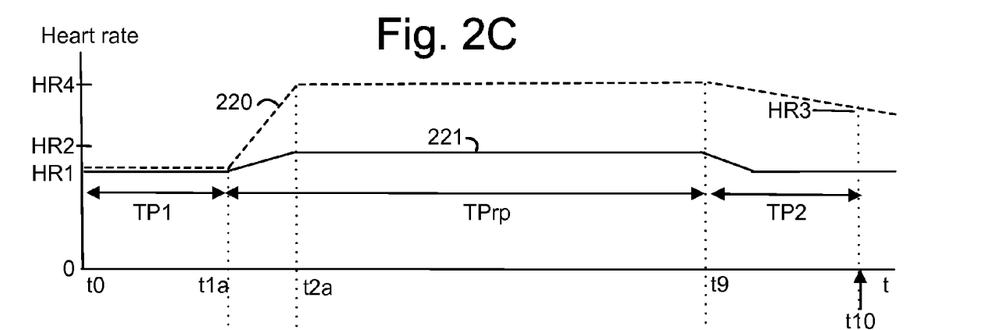
FIG. 2C depicts example heart rate values 220 corresponding to the high activity of FIG. 2A, and a plot 221 of example heart rate values corresponding to the low activity of FIG. 2B.

FIG. 2C depicts a plot 220 of example heart rate values corresponding to the high activity of FIG. 2A, and a plot 221 of example heart rate values corresponding to the low activity of FIG. 2B. These plots are not known by the activity monitor, in one approach, but are provided for understanding. As mentioned, some form of repetitive activity is detected in a time period of t1a-t9. Plot 221 represents a heart rate which yields the same calorie consumption as determines based on the activity. In this case, the heart rate is initially at HR1 then peaks at HR2. Plot 220 represents an actual heart rate of the user. The user obtains a heart rate reading of HR3 (e.g., 110 bpm) at t10. In this case, the heart rate is initially at HR1 then peaks at HR4. The heart rate decreases gradually when the strenuous exercise stops at t9 and reaches HR3 at t10. The rate of decrease in the heart rate for an individual user after the user stops an activity can be determined. Thus, knowing that the heart rate is HR3 at t10, and knowing that the activity stopped at t9, the amount of decay D in the heart rate can be determined. HR4 can be determined from HR3+D.

Figure 2D:
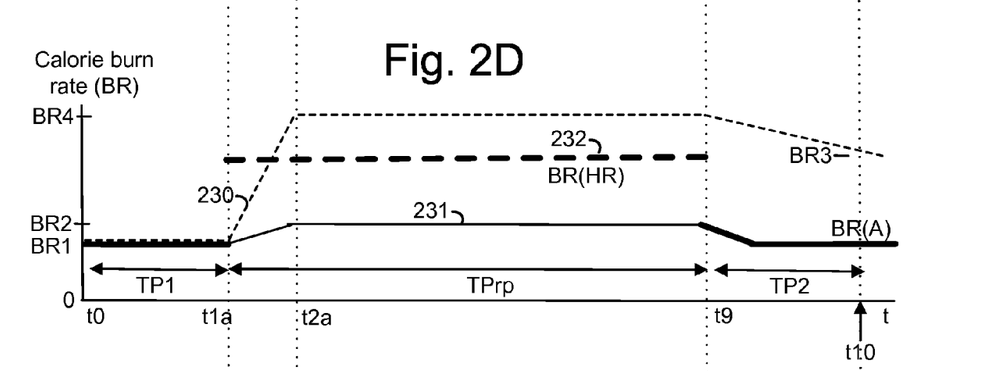
FIG. 2D depicts a plot 230 of example calorie burn rates corresponding to the high activity of FIG. 2A, and a plot 231 of example calorie burn rates corresponding to the low activity of FIG. 2B.

FIG. 2D depicts a plot 230 of example calorie burn rates corresponding to the high activity of FIG. 2A, and a plot 231 of example calorie burn rates corresponding to the low activity of FIG. 2B. The calorie burn rate can be a function of time. The plot 231 may be recorded by the activity monitor while the plot 230 is not known to the activity monitor, in one approach, but is provided for understanding.

Figure 2E:
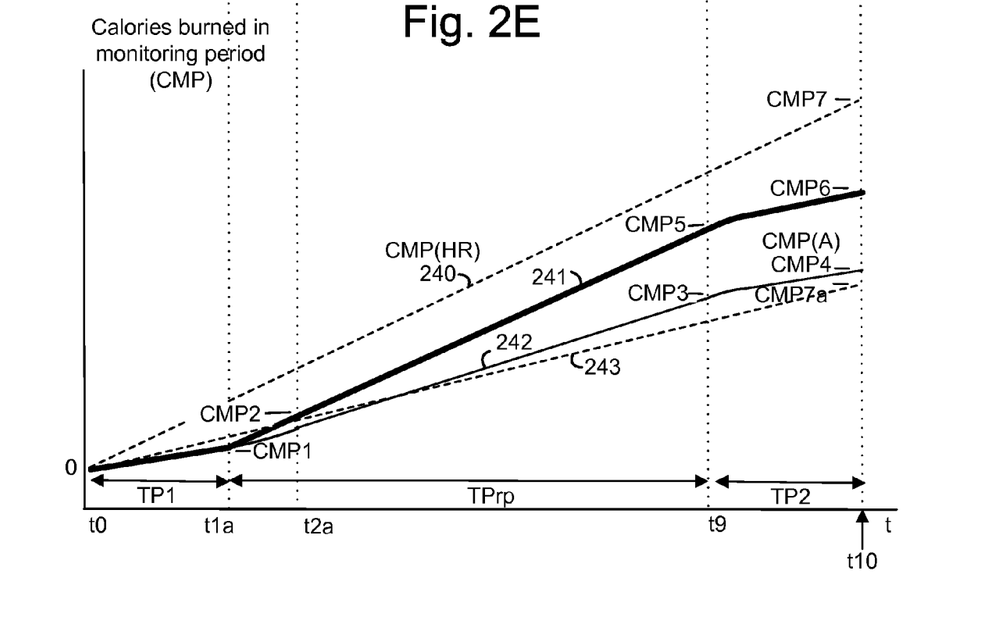
FIG. 2E depicts a plot 240 of cumulative calories burned based on the high calorie burn rate 230 of FIG. 2D, and a plot 242 of cumulative calories burned based on the plot 231 of lower calorie burn rate of FIG. 2D.

Plot 230 indicates that a burn rate of BR1 applies from t0-t1a, a burn rate of BR4 applies from t2a-t9, and a burn rate of BR3 applies at t10. For example, the data of FIG. 3C can be referenced to determine that BR3 correlates with HR3, the heart rate reading. A burn rate based on the measured heart rate BR(HR) is set to BR3. A burn rate based on the activity BR(A) is BR1 from t0-t1a, increases to BR2 from t1a-t2a, is at BR2 from t2a-t9, decreases to BR1 after t9 and is at BR1 until t10. Line 232 represents BR(HR). The heavy lines indicate the burn rate which is used to determine calories consumption. Essentially, BR(HR) is substituted for BR(A) during TPrp and BR(A) is used at other times (e.g., TP1 and TP2), in one approach. It is assumed that BR(HR) provides a more accurate representation of the burn rate than BR(A) during the period of repetitive activity. FIG. 2E depicts a plot 240 of cumulative calories burned based on the plot 230 of high calorie burn rate of FIG. 2D, and a plot 242 of cumulative calories burned based on the plot 231 of lower calorie burn rate of FIG. 2D. The cumulative calories burned is obtained by integrating the burn rate over time. CMP(HR) represents the calories burned based on the heart rate measurement at t10. Specifically, assuming BR3 applies over the time period t10-t0, the cumulative calories burned at t10 is BR3× (t10-t0)=CMP7. CMP(A) represents the calories burned based on the activity level. It starts at 0, reaches a value CMP1 at t1a, reaches a value CMP3 at t9 and reaches a value CMP4 at t10. In this example, CMP(HR)>CMP(A) (e.g., CMP7>CMP4) at t10. A heavy line 241 represents a cumulative calories burned which is obtained by applying the burn rate BR(HR) in place of the burn rate BR(A) during TPrp. As can be seen, the slope of the plot 241 matches that of the plot 240 during TPrp. In contrast, the slope of the plot 242 is lower than that of the plot 240 during TP1 and TP2. After TPrp, in TP2, the slope of the plot 241 matches that of the plot 242. CMP6 is the cumulative amount of calories burned (e.g., 400 calories) which is output to the user. Essentially, CMP(A) receives a boost based on the heart rate to provide a more realistic result. If the heart rate was not considered, a lower CMP of CMP4 would be output instead.

A line 243 provides another example of CMP(HR), where CMP(HR)<CMP(A) (e.g., CMP7a<CMP4) at t10. For example, if the user has performed a repetitive activity which is not very strenuous, such as waving the arms back and forth, the heart rate reading will be relatively low, resulting in a lower burn rate and cumulative calories burned. Also, if the user performs a strenuous repetitive activity but waits a relatively long time to take the heart rate reading, it will be relatively low.

Figure 2F:
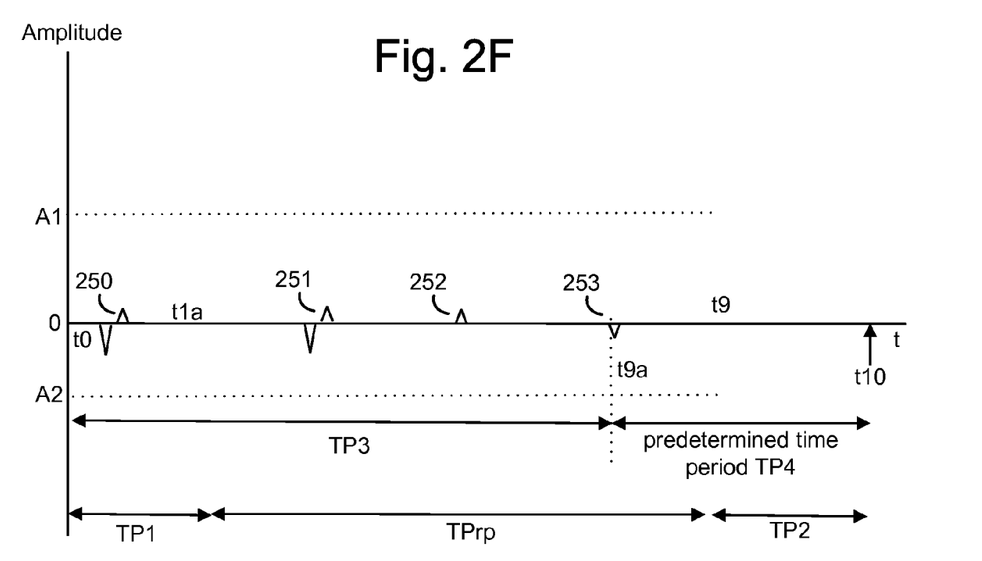
FIG. 2F depicts example accelerometer readings during strength training exercises, showing little or no activity, where a repetitive pattern is not detected.

FIG. 2F depicts example accelerometer readings during strength training exercises, showing little or no activity, where a repetitive pattern is not detected. In this example, accelerometer readings 250-253 indicate little or no activity. However, the user may still be exercising strenuously. For example, little or no activity may be sensed by the accelerometer during various strength training exercises or during other exercise, e.g., riding a stationary bicycle, in which the activity monitor is essentially not moving. When the heart rate is measured at t10 and is relatively high, it can be concluded that the user has in fact been exercising vigorously, so that the calorie expenditure which is determined by the accelerometer readings alone would underestimate the calorie expenditure. However, the specific period of the vigorous exercise may not be known since the period of exercise may not be detectable within a longer monitoring period. In this situation, a reasonable compromise is to assume that a calorie burn rate based on the heart rate applies over a predetermined period (TP) immediately before the heart rate measurement at t10. As an example, ten minutes can be used. Another approach is for the activity monitor to prompt the user with a message such as: Your heart rate is 100 bpm. How long have you been exercising? The user can then enter a time period, e.g., 20 minutes, and a calorie burn rate based on the heart rate is applied over the entered time period.

Figure 2G:
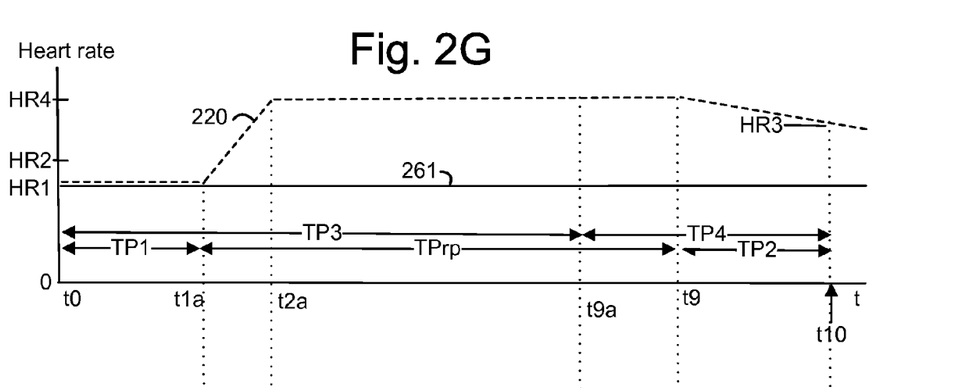
FIG. 2G depicts example heart rate values 220 corresponding to the high activity of FIG. 2A, and example heart rate values 261 corresponding to FIG. 2F.

FIG. 2G depicts a plot 220 of example the heart rate values corresponding to the high activity of FIG. 2A, and a plot 261 of example heart rate values corresponding to FIG. 2F. Here, the activity measurements indicate essentially no activity, corresponding to a fixed heart rate at HR1 (plot 261). Plot 220 is the same as discussed previously, as an assumption. As before, these plots are not known by the activity monitor, in one approach, but are provided for understanding.

Figure 2H:
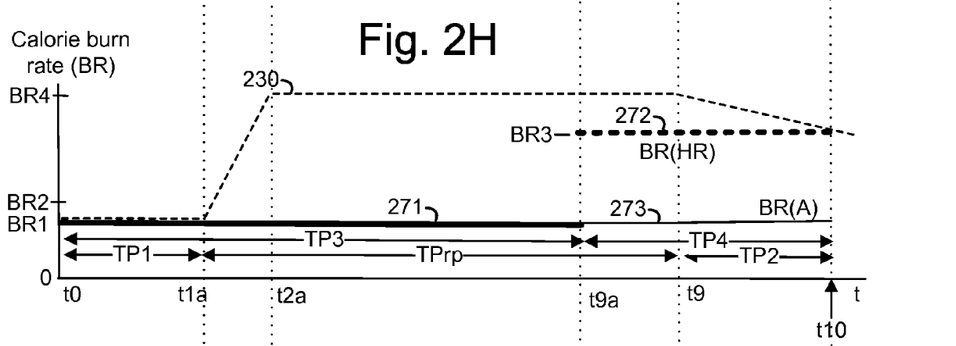
FIG. 2H depicts the plot 230 of example calorie burn rates corresponding to the high activity of FIG. 2A, and example plots 271 and 273 of calorie burn rates corresponding to FIG. 2F.

FIG. 2H depicts the plot 230 of example calorie burn rates corresponding to the high activity of FIG. 2A, and example plots 271 and 273 of calorie burn rates corresponding to FIG. 2F. Plot 230 is the same as discussed previously. The heavy lines indicate the applicable burn rate. Plot 271 represents a burn rate BR(A)=BR1 which applies during TP3, a remainder of the monitoring period. Line 272 represents a burn rate BR(HR)=BR3 which applies during TP4.

Figure 2I:
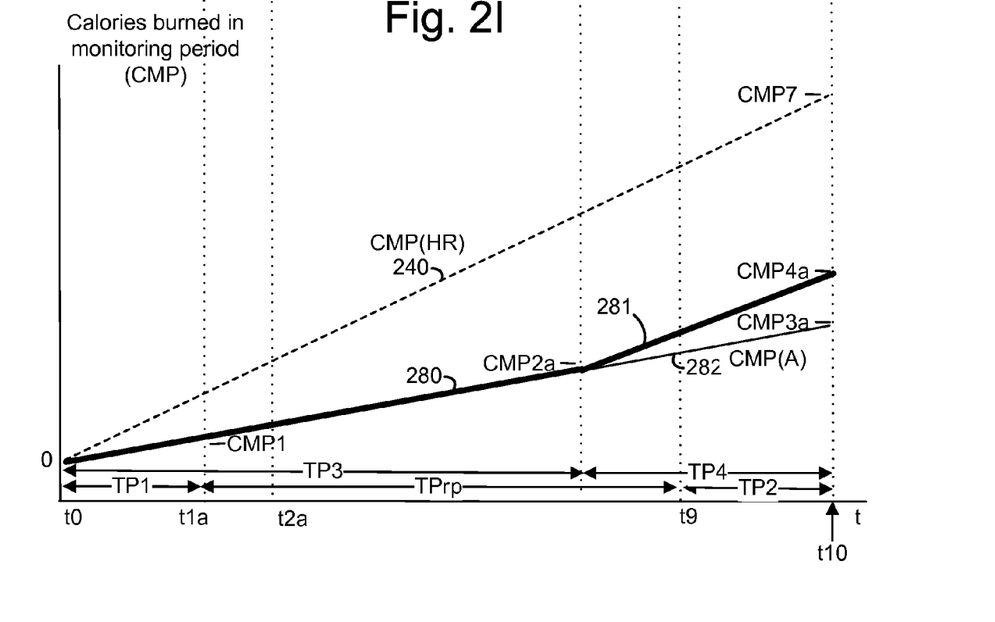
FIG. 2I depicts the plot 240 of cumulative calories burned based on the plot 230 of high calorie burn rate of FIG. 2D, and plots 280 and 282 of cumulative calories burned based on the plots 271 and 273 of calorie burn rates of FIG. 2H.

FIG. 2I depicts the plot 240 of cumulative calories burned based on the plot 230 of high calorie burn rate of FIG. 2D, and plots 280 and 282 of cumulative calories burned based on the plots 271 and 273 of calorie burn rates of FIG. 2H. Plot 240 is the same as discussed previously. CMP(HR) represents the calories burned based on the heart rate measurement at t10. CMP(A) represents the calories burned based on the activity level. It starts at 0, reaches a value CMP1 at t1a, reaches a value CMP2a at t9a and reaches a value CMP3a at t10. The slope is fixed. A heavy line 241 represents a cumulative calories burned which is obtained by applying the burn rate BR(HR) in place of the burn rate BR(A) during TP4. The burn rate BR(A) applies during TP3.

As can be seen, the slope of the plot 281 matches that of the plot 240 during TPrp. In contrast, the slope of the line 280 is lower than that of the plot 240 during TP3 and is based on the burn rate of plot 272. CMP4a is the cumulative amount of calories burned which is output to the user. Essentially, CMP(A) receives a boost to provide a more realistic result. If the heart rate was not considered, a lower CMP of CMP3a would be output instead.

Figure 3A:
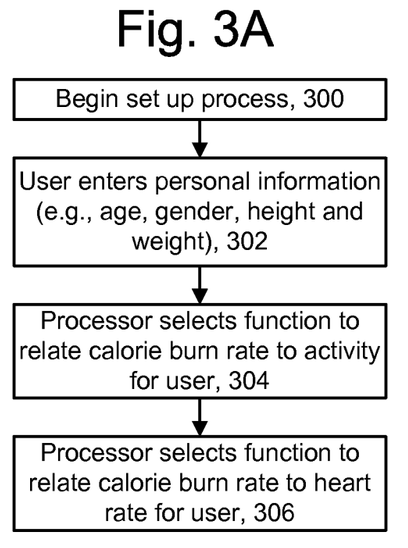
FIG. 3A depicts a setup process for the activity monitor of FIG. 1A.
Figure 3B:
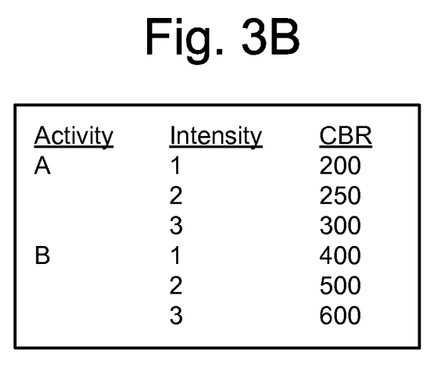
FIG. 3B depicts a relationship between activity type and calorie burn rate in accordance with step 304 of FIG. 3A.
Figure 3C:
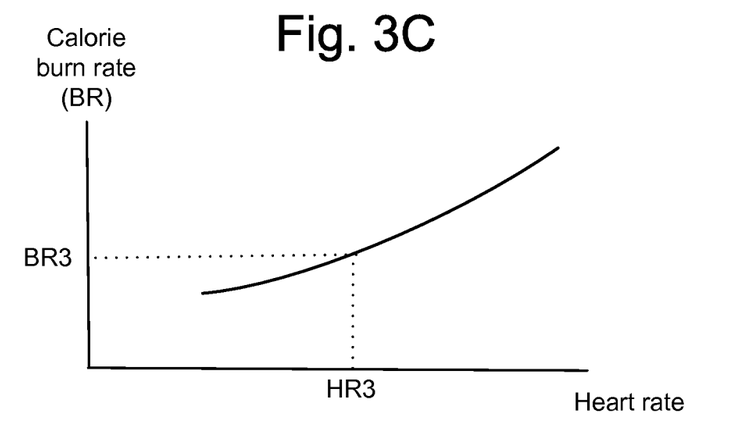
FIG. 3C depicts a relationship between calorie burn rate and heart rate in accordance with step 306 of FIG. 3A.

FIG. 3A depicts a setup process for the activity monitor of FIG. 1A. At step 300, the setup process begins. For example, the user may use the mode select button 105 to enter information such as by scrolling through menus. At step 302, the user enters personal information (e.g., age, gender, height and weight). In another approach, the activity monitor can communicate with a host computing device which provides a user interface. At step 304, the processor selects a function to relate calorie burn rate to activity for user. For example, see FIG. 3B which depicts a relationship between activity type and calorie burn rate. In a simplified example, different activities, e.g., Activity 1 or 2, and different intensities, e.g., 1, 2 and 3 can be associated with calorie burn rates (CBR). Calorie burn rates can be provided for repetitive activities such as certain exercises and non-repetitive activities such as sleeping and sitting. At step 306, the processor selects a function to relate calorie burn rate to heart rate for the user. For example, see FIG. 3C which depicts a relationship between calorie burn rate and heart rate. For instance, the heart rate HR3 discussed previously corresponds to a burn rate BR3.

Figure 3D:
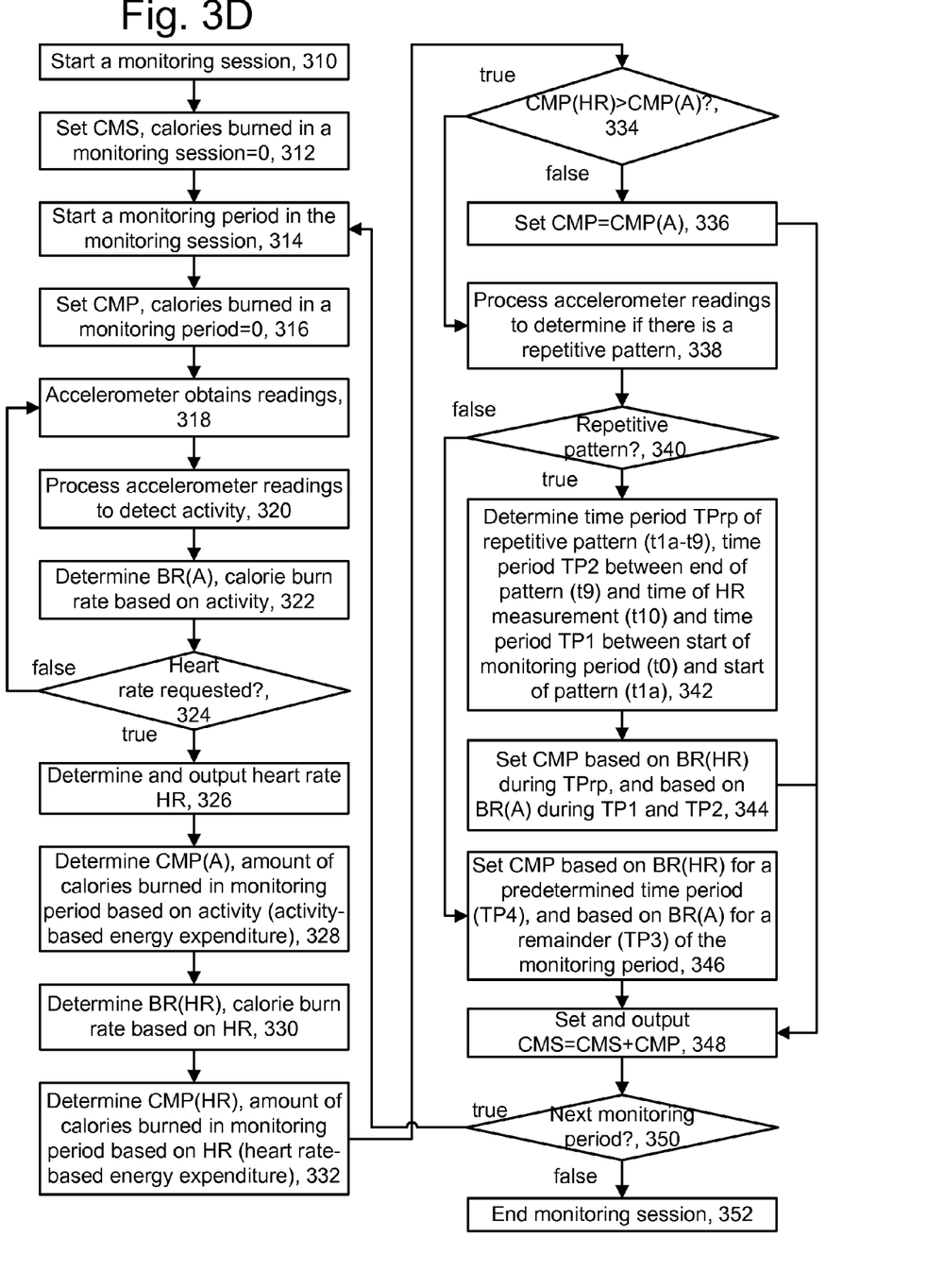
FIG. 3D depicts an operational mode for the activity monitor of FIG. 1A.

FIG. 3D depicts an operational mode for the activity monitor of FIG. 1A. A monitoring session can be a relatively long period such as hours or days in which data is gathered. A monitoring period can be a shorter period which is a time between heart rate measurements. A monitoring session can have multiple monitoring periods. For example, a user may choose to obtain a heart rate reading every few minutes during an exercise session and less frequently during other activates. The steps include: start a monitoring session, 310; set CMS, calories burned in a monitoring session=0, 312; start a monitoring period in the monitoring session, 314; set CMP, calories burned in a monitoring period=0, 316; accelerometer obtains readings, 318; process accelerometer readings to detect activity, 320; and determine BR(A), calorie burn rate based on activity, 322.

Decision step 324 determines if a heart rate reading has been requested by the user. If decision step 324 is false, step 318 is repeated. If decision step 324 is true, additional steps include: determine and output heart rate HR, 326; determine CMP(A), amount of calories burned in monitoring period based on activity (activity-based energy expenditure), 328; determine BR(HR), calorie burn rate based on HR, 330; and determine CMP(HR), amount of calories burned in monitoring period based on HR (heart rate-based energy expenditure), 332.

Decision step 334 determines if CMP(HR)>CMP(A). If decision step 334 is false, step 336 sets CMP=CMP(A). If decision step 334 is true, step 338 processes the accelerometer readings to determine if there is a repetitive pattern.

Decision step 340 determines if there is a repetitive pattern. If decision step 340 is false, step 346 sets CMP based on BR(HR) for a predetermined time period (TP4), and based on BR(A) for a remainder (TP3) of the monitoring period. If decision step 340 is true, step 342 determines a time period TPrp of the repetitive pattern (t1a-t9), a time period TP2 between the end of pattern (t9) and a time of the HR measurement (t10) and time period TP1 between the start of the monitoring period (t0) and the start of pattern (t1a). Step 344 sets CMP based on BR(HR) during TPrp, and based on BR(A) during TP1 and TP2. Step 346 is then reached as discussed. Step 348 sets and outputs, e.g., via the display, CMS=CMS+CMP. This is the amount of calories burned in the monitoring session. For example, a cumulative total of calories burned can be provided over the course of hours or days. In one approach, the cumulative total of calories can be repeatedly updated, e.g., once every few seconds. When a heart rate reading is taken and this results in a boost to the cumulative total, the cumulative total can be updated in a step increase, e.g., from 400 to 450 calories. The activity monitor could provide a message or other notification to the user to inform him that the cumulative total has been boosted. This notification could continue for several minutes, for example. A record of such notifications could also be recalled by the user.

Decision step 350 determines if there is a next monitoring period. Typically, this is true unless the user enters a command to end the monitoring session at step 352. Step 314 follows if decision step 350 is true.

Generally, data regarding calorie expenditures can be viewed on the display and/or uploaded to an online service for viewing and further analysis. Energy expenditure can be expressed in terms of calories, Joules or other measure. Energy expenditure can represent a burn rate and/or cumulative amount of calories.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto.

What is claimed is:

1. An activity monitor, comprising:
   an accelerometer, the accelerometer is configured to provide readings which indicate a frequency and magnitude of movement of a user;
   an on-demand ECG based heart rate monitor including a plurality of electrodes, the on-demand heart rate monitor is touch-activated based on a touch of the user;
   a display device;
   a processor, the processor is communicatively coupled to the accelerometer, the on-demand heart rate monitor and the display device; and
   a memory, wherein the accelerometer, the heart rate monitor, the display device, the processor and a memory are housed within the activity monitor and the memory is configured to store code that, when executed by the processor, is configured to:
   process the readings of the accelerometer to determine an amount of activity of the user, the activity is during a period, wherein the amount of activity is proportional to the frequency and magnitude of movement of the user;
   determine an activity-based calorie burn rate based on the amount of activity,
   determine an activity-based calorie expenditure by applying the activity-based calorie burn rate over the period,
   set an output calorie expenditure on the display device based on the activity-based calorie expenditure, and
   in response to a touch activation of the on-demand heart rate monitor at an end of the period:
   obtain a heart rate measurement of the user,
   determine a heart rate-based calorie burn rate based on the heart rate measurement, determine a heart rate-based calorie expenditure by applying the heart rate-based calorie burn rate over the period,
   if the heart rate-based calorie expenditure exceeds the activity-based calorie expenditure, determine one portion of the period to apply the heart rate-based calorie burn rate and another portion of the period to apply the activity-based calorie burn rate, determine a first calorie expenditure by applying the heart rate-based calorie burn rate but not the activity-based calorie burn rate over the one portion of the period, determine a second calorie expenditure by applying the activity-based calorie burn rate but not the heart rate-based calorie burn rate over the another portion of the period, determine a sum of the first calorie expenditure and the second calorie expenditure, and boost the output calorie expenditure on the display device to the sum, and if the heart rate-based calorie expenditure does not exceed the activity-based calorie expenditure, do not boost the output calorie expenditure on the display device.

2. The activity monitor of claim 1, wherein the memory stores code that, when executed by the processor, is configured to:
determine a duration of the one portion of the period as a duration in which the movement of the user is repetitive and the magnitude of the movement of the user is below a first level; and
determine a duration of the another portion of the period as a duration in which the movement of the user is repetitive and the magnitude of the movement of the user is above the first level.

3. The activity monitor of claim 2, wherein:
the movement of the user which is measured by the accelerometer comprises accelerations of the user; and
the memory stores code that, when executed by the processor, is configured to evaluate the accelerations to determine that the magnitude of the movement of the user is below the first level and the movement of the user is repetitive in the one portion of the period, and to determine that the magnitude of the movement of the user is above the first level and the movement of the user is repetitive in the another portion of the period.

4. The activity monitor of claim 2, wherein:
the movement of the user which is measured by the accelerometer comprises accelerations of the user; and
the memory stores code that, when executed by the processor is configured to evaluate a number of zero crossings of the accelerations to determine that the movement of the user is repetitive in the one portion of the period and in the another portion of the period.

5. The activity monitor of claim 1, wherein the memory stores code that, when executed by the processor, is configured to:
determine that a repetitive pattern is not detected in the readings of the accelerometer, and in response, set the one portion of the period as a predetermined period which is immediately before the heart rate measurement.

6. The activity monitor of claim 1, wherein the memory stores code that, when executed by the processor, is configured to:
determine that the movement of the user indicates the user has performed strength training during the one portion of the period.

7. The activity monitor of claim 1, wherein:
the movement of the user which is measured by the accelerometer comprises accelerations of the user; and
the memory stores code that, when executed by the processor is configured to determine the activity-based calorie burn rate based on at least one of a frequency, a magnitude or a number of zero crossings of the accelerations.

8. The activity monitor of claim 1, wherein:
the on-demand heart rate monitor comprises an ECG heart rate monitor comprising a plurality of electrodes.

9. The activity monitor of claim 1, wherein the memory stores code that, when executed by the processor, is configured to:
set the one portion of the period as a predetermined period which is immediately before the heart rate measurement.

10. The activity monitor of claim 1, wherein the memory stores code that, when executed by the processor, is configured to:
determine a duration of the one portion of the period as a duration in which the movement of the user is consistent with weight lifting.

11. The activity monitor of claim 1, wherein the memory stores code that, when executed by the processor, is configured to:
if the heart rate-based calorie expenditure exceeds the activity-based calorie expenditure, provide a notification to the user which informs the user that the output calorie expenditure on the display device has been boosted.

12. The activity monitor of claim 11, wherein the memory stores code that, when executed by the processor, is configured to:
maintain a record of the notification and recall the notification for the user.

13. The activity monitor of claim 1, wherein the memory stores code that, when executed by the processor, is configured to:
if the heart rate-based calorie expenditure exceeds the activity-based calorie expenditure, prompt the user to enter a time period in which the user has been exercising and set the one portion of the period as the time period entered by the user.

* * * * *